United States Patent [19]

Cheney et al.

[11] Patent Number: 5,365,018
[45] Date of Patent: Nov. 15, 1994

[54] METHOD OF CAUSING SOMATIC HYBRIDIZATION BETWEEN TWO SPECIES OF ALGAE

[75] Inventors: Donald P. Cheney, Ipswich; Le Z. Wang, Boston, both of Mass.

[73] Assignee: Northeastern University, Boston, Mass.

[21] Appl. No.: 40,625

[22] Filed: Mar. 31, 1993

[51] Int. Cl.$^5$ .................. C12N 15/00; C12N 5/00; C12N 5/02; A01G 7/00
[52] U.S. Cl. .................. 800/220; 800/200; 800/DIG. 7; 800/240; 47/1.4; 47/58; 435/172.1; 435/172.2; 435/240.45; 935/93; 935/94; 935/96; 935/98
[58] Field of Search ............ 435/172.1, 172.2, 240.4, 435/240.49, 240.45; 800/200, 220, 240, DIG. 7; 935/91, 98, 93, 94, 96; 47/1.401, 58.05, 1.4

[56] References Cited

U.S. PATENT DOCUMENTS

| 4,199,895 | 4/1980 | Avron et al. ............ 47/1.4 |
| 4,869,017 | 9/1989 | Bird et al. ............ 47/1.4 |
| 4,996,389 | 2/1991 | Bird ............ 800/200 |

OTHER PUBLICATIONS

J. Phycol. "The Role of Secondary Pit Connections in Red Algal Parasitism" by Lynda J. Goff, et al., pp. 483–508, 1985.
The Korean Journal of Phycology "Wound–Healing in Several Filamentous Red Algae, Ceramiales", vol. 3, No. 1, pp. 15–27, 1988.
Botanica Marina "Wound Healing in Cultured *Eucheuma alvarezii* var. *tambalong* Doty", by R. Azanza-Corrales, et al., vol. 32, pp. 229–234, 1989.
Hydrobiologia "Calluses and Callus–Like Growth in Seaweeds: Induction and Culture", by M. Polne-Fuller, et al., pp. 131–238, 1987.
Journal of Applied Phycology "Branch, Micropropagule and Tissue Culture of the Red Algae *Eucheuma denticulatum* and *Kappaphycus alvarezii* Farmed in the Philippines", by C. J. Dawes, et al. pp. 247–257, 1991.
Protoplasma "Cytoplasmic Incompatibility Following Somatic Cell Fusion in *Griffithsia pacifica* Kylin, a Red Alga", by D. J. Koslowsky, et al., pp. 7–17, 1984.
Hydrobiologia "Carrageenan Analysis of Tissue Cultures and Whole Plants of *Agardhiella subulata*", by D. P. Cheney, et al., pp. 161–166, 1987.
Hydrobiologia "Some Effects of Plant Growth Regulators on Tissue Cultures of the Marine Red Alga *Agardhiella subulata* (Gigartinales, Phodophyta)", by P. M. Bradley, et al., pp. 353–360, 1990.
Annals New York Academy of Sciences "Nuclear Transfer from Parasite to Host", by L. J. Goff, et al., pp. 402–423, 1987.
"Parasexually Produced Hybrids Between Female and Male Plants of *Griffithsia tenuis* C. Agardh, A Red Alga", by S. D. Waaland, pp. 65–68, 1978.
J. Phycol. "Regeneration and Sexual Differentiation of *Griffithsia japonic* (Ceramiaceae, Rhodophyta) Through Somatic Cell Fusion", by M. S. Hwag, et al., pp. 441–447, 1991.
N. Saga et al. (1986) Fisheries Agency of Japan 83:37–43 (abstract).

Primary Examiner—David T. Fox
Assistant Examiner—Bruce R. Campbell
Attorney, Agent, or Firm—Weingarten, Schurgin, Gagnebin & Hayes

[57] ABSTRACT

A method of causing somatic cell hybridization between two species of non-filamentous algae by growing somatic algal tissue from each of the two species of algae in close proximity, in a nutrient solution, and isolating and culturing the hybrid somatic shoots that form.

9 Claims, 10 Drawing Sheets

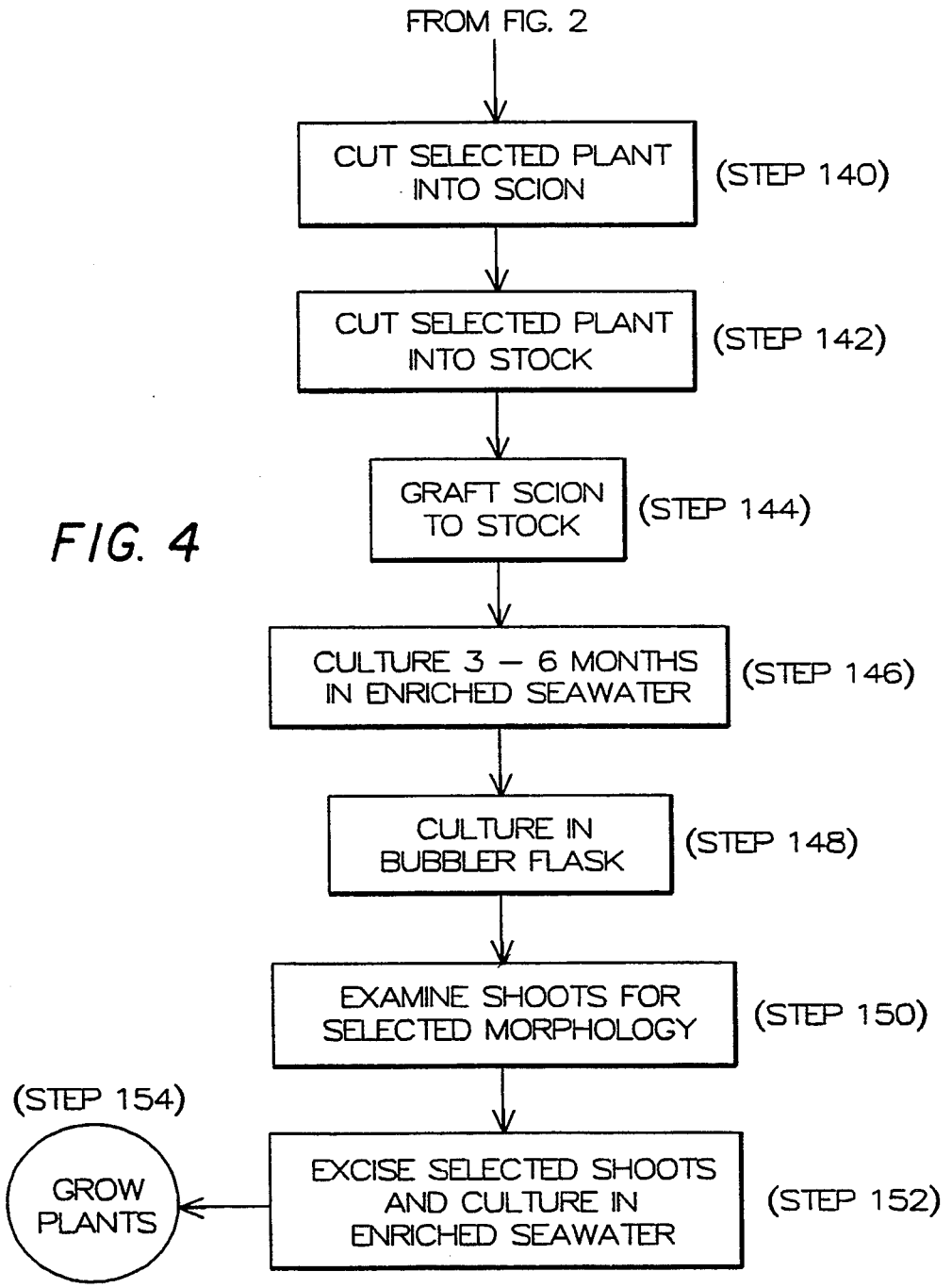

METHOD OF CAUSING SOMATIC HYBRIDIZATION BETWEEN TWO SPECIES OF ALGAE

FIELD OF THE INVENTION

The invention relates to the field of algae culture and more particularly to the field of algal culture techniques for causing somatic cell hybridization in algae.

BACKGROUND OF THE INVENTION

Economically important phycocolloids such as carrageenan and agar are produced by certain red algae. To extract a phycocolloid of interest, an alga is grown in a marine environment, is harvested and is processed. Different algal species may produce phycocolloids having different chemical properties and different physical characteristics, and/or may grow at an increased growth rate.

For example, carrageenan, a food industry colloid used as a clarifying agent, a suspending agent or a crystallization controlling agent, is a mixture of various length chains of sulfated disaccharide subunits. Different species of algae produce carrageenan chains having a different average number of sulphate groups per disaccharide subunit. The average sulfation per disaccharide typically varies from one (designated κ carrageenan) to three (designated λ carrageenan) sulfates per disaccharide. The intermediate value of two sulfates per disaccharide is designated ι carrageenan. The degree of sulfation determines the gel strength of the colloid extracted. A decrease in sulfation results in an increase in gel strength. Different gel strengths are desirable for different applications.

The ability to modify one species of algae by hybridizing the genetic material of a second species would permit the characteristics of the phycocolloid produced by the second species to be exhibited by the first species. Thus, for example, carrageenan having a higher than normal gel strength could be produced by an alga which typically produces a low or intermediate gel strength carrageenan. However, typically only closely related strains of a single species can sexually exchange genetic material successfully. Hence sexual hybridization has not produced commercially useful hybrid algae.

A number of techniques have been developed to create hybrid cells by fusing somatic cells. Referring to FIG. 1, Hwang et al. in *Regeneration and Sexual Differentiation of Griffithsia japonica (Ceramiaceae, Rhodophyta) Through Somatic Cell Fusion*, J. Phycol. 27, 441–447 (1991), describe a method for the somatic cell fusion of cells of the filamentous red alga *Griffithsia japonica*, by wound healing, so as to form a hybrid cell. In this technique 10, a cell 14 near the apical cell is wounded (step 16) and the cytoplasm removed. Within ten hours, adjacent cells 18 produce (step 22) repair cells 20 which grow into the lumen 21 of the wounded cell 14. The wounded cell is then transected (step 24) and the separated filaments are immobilized in close contact on an agar plate (step 26). The repair cells 20 fuse (step 30), forming a hybrid cell 32 which can then be isolated (step 34) and cultured.

Similarly, referring to FIG. 1a, Susan D. Waaland in *Parasexually Produced Hybrids between female and Male Plants of Griffithsia tenuis C. Agardh, a Red Alga*, Planta 138, 65–68 (1978) describes the somatic cell fusion of male and female somatic cells of the filamentous red alga *Griffithsia tenuis* grown within a thin cylinder formed from the walls of the green alga Nitella. In this technique 36, two filaments 40, 40a are positioned (step 38) within the thin cylinder 42 and allowed to grow. The upper filament 40 produces (step 44) a rhizoid 46, while the lower filament produces a repair cell 48. The rhizoid 46 and the repair cell 48 grow toward one another. Eventually the rhizoid 46 and the repair cell 48 fuse (step 50) to form a hybrid cell 52, which can then be isolated and cultured. Thus both the Hwang and Waaland techniques of somatic cell fusion are limited to the fusion of cells of filamentous algae of a single genus.

Bradley and Cheney in *Some Effects of Plant Growth Regulators on tissue cultures of the marine red alga Agardhiella subulata (Gigartihales, Rhodophyta)*, Hydrobiologica 204/205: 353–360, 1990, describe tissue culture by the growing of projections and calluses from a disk cut from red algae but do not describe any technique for creating somatic cell hybrids.

The present invention relates to somatic cell hybridization technique which are applicable to non-filamentous algae. The new techniques accomplish somatic cell hybridization of varieties of non-filamentous algae which have significant commercial value.

SUMMARY OF THE INVENTION

The invention relates to a method of forming somatic hybrids from two strains of non-filamentous algae. Tissue from each of the non-filamentous algae are grown in close proximity in a culture medium. The hybrid somatic shoots that form are then isolated and cultured. In one embodiment a piece of tissue from each of the non-filamentous algal strains to be hybridized are affixed in close juxtaposition in a culture medium and the hybrid heterokaryon structures which form are isolated and individually cultured. In another embodiment, a scion from one strain of non-filamentous algae is grafted onto a second strain of non-filamentous algae and the resulting graft is grown in a culture medium. The hybrid heterokaryon shoots which form from the graft are then isolated and individually cultured.

BRIEF DESCRIPTION OF THE DRAWING

Other features and benefits of the invention can be more clearly understood with reference to the specification and the accompanying drawings in which:

FIG. 4 is a flow chart of the steps in one embodiment of the method of the invention for the somatic cell hybridization of non-filamentous algae utilizing grafting;

DESCRIPTION OF THE PREFERRED EMBODIMENT

Figures 1, 1A:
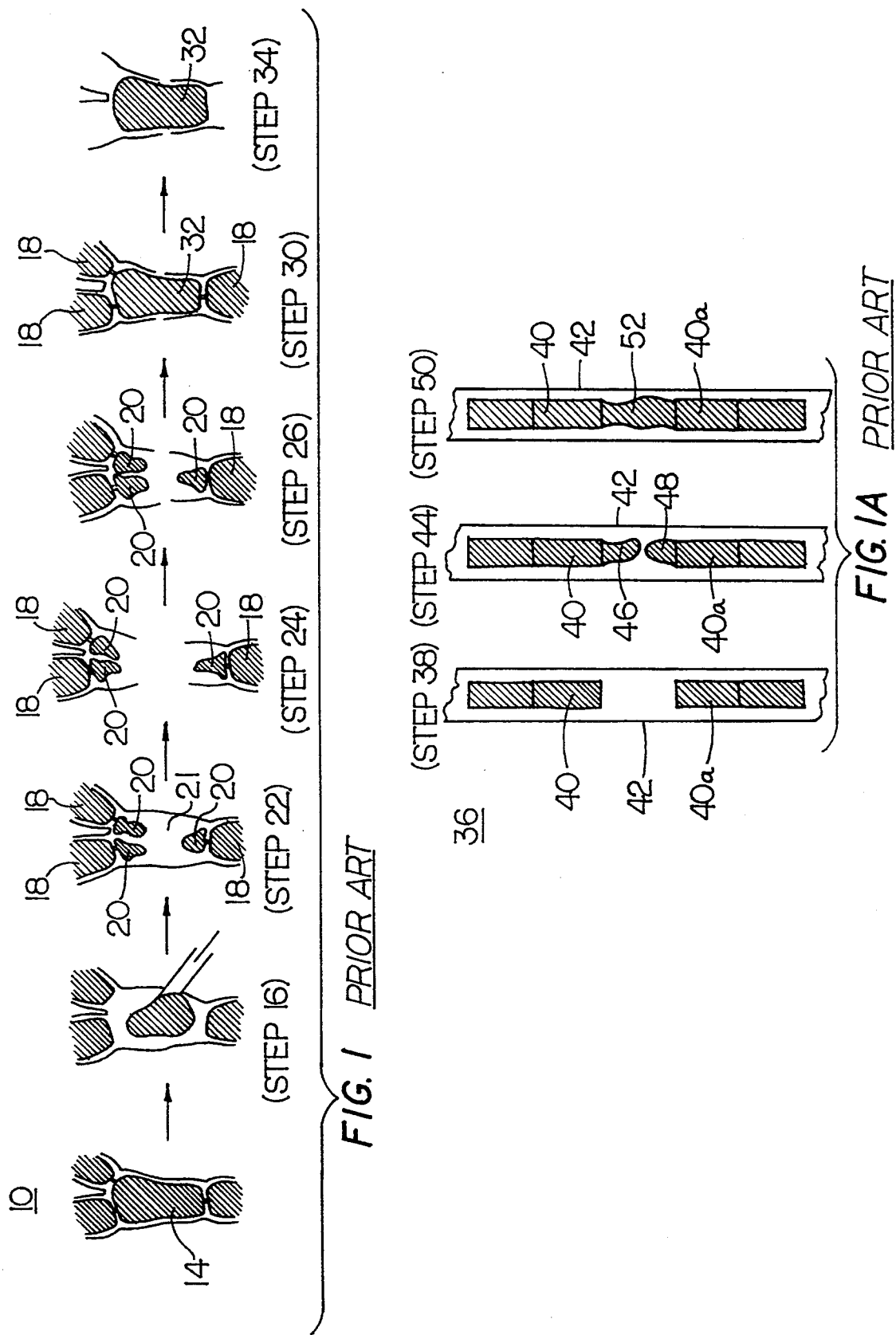
FIG. 1 is a diagrammatic representation of the steps used in one technique of fusing filamentous algae as known to the prior art.
FIG. 1a is a diagrammatic representation of the steps used in another technique of fusing filamentous algae as known to the prior art.
Figure 2:
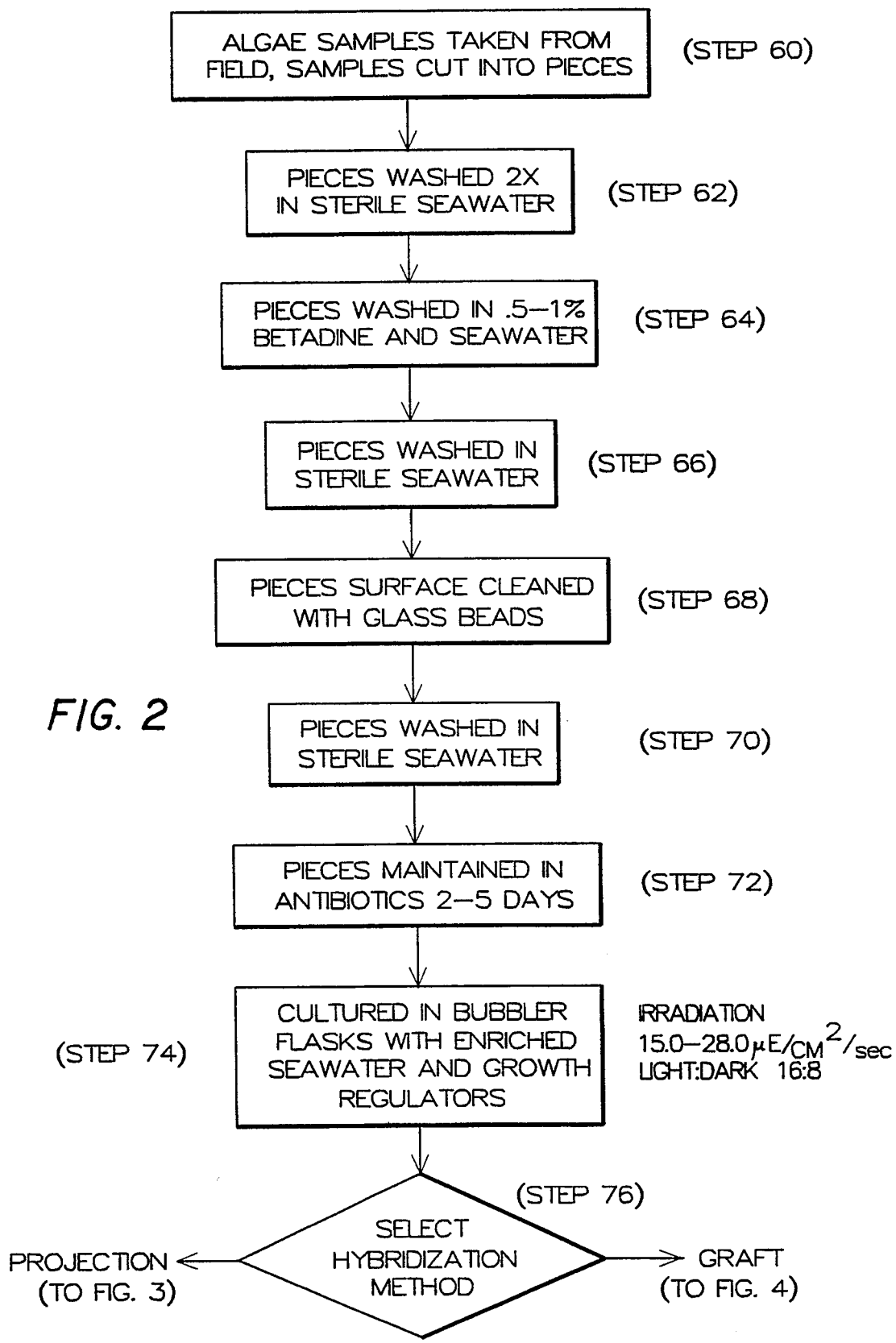
FIG. 2 is a flow chart of the initial steps in one embodiment of the method of somatic cell hybridization of the invention.

Referring to FIG. 2, the two species of non-filamentous algae which are to be hybridized are taken from the field and sliced into small pieces (step 60). The pieces are then washed once or twice in autoclaved or filter-sterilized seawater (step 62). (Seawater obtained from either sterilization technique hereinafter is referred to collectively as sterilized seawater.) The sliced algal pieces are then dipped into a 0.5–1% Betadine and seawater solution for 1–2 minutes (step 64) and the algal pieces are again rewashed with sterilized seawater (step 66).

To remove any surface contaminants from the algal pieces, a number of algal pieces are placed into a 300 ml flask with 1–3 grams of 0.5 mm diameter glass beads and a small amount of sterilized seawater. The flask containing the beads, seawater and algal pieces is then strongly shaken for several minutes (step 68).

The algal pieces are then removed from the flask, washed again three to five times with sterilized seawater (step 70), and maintained in antibiotics (in one embodiment an antibiotic mixture termed E3) for two to five days (step 72). The antibiotic mixture E3 used in the medium consists of 30 $\mu$g/ml each of polymyxin B, nalidixic acid, erythromycin, colistin, vancomycin, ampicillin, trimethoprim, and chlortetracycline.

Once the E3 antibiotic treatment of the algal pieces is complete, each algal species is incubated in a respective bubbler flask at an approximate temperature of 20° C.–29° C. (for tropical algae) in half (ESS/2) or quarter concentration (ESS/4) enriched seawater (ESS) or in ASP12 artificial seawater. In one embodiment, the plant growth regulators consist of a mixture of 5.4 nM–53.7 $\mu$M $\alpha$-naphthaleneacetic acid (NAA) and 4.6 nM–45.6 $\mu$M zeatin, with an especially preferred embodiment consisting of a final concentration of 0.01 ppm $\alpha$-naphthaleneacetic acid and 0.01 ppm zeatin in the EES.

During culture in the bubbler flasks, each algal species is irradiated by cool-white fluorescent light at an intensity of 15.0–28.0 $\mu$E/cm$^2$/sec with a light:dark cycle of 16:8 hours (step 74). The algal species are allowed to grow for at least a week under these conditions to permit the plants to adapt to the environment and to insure that the plants are free of contaminants. The medium in the bubbler flasks is changed weekly. At this point, the plants to be hybridized may be selected and the method of hybridization begun.

Figure 3:
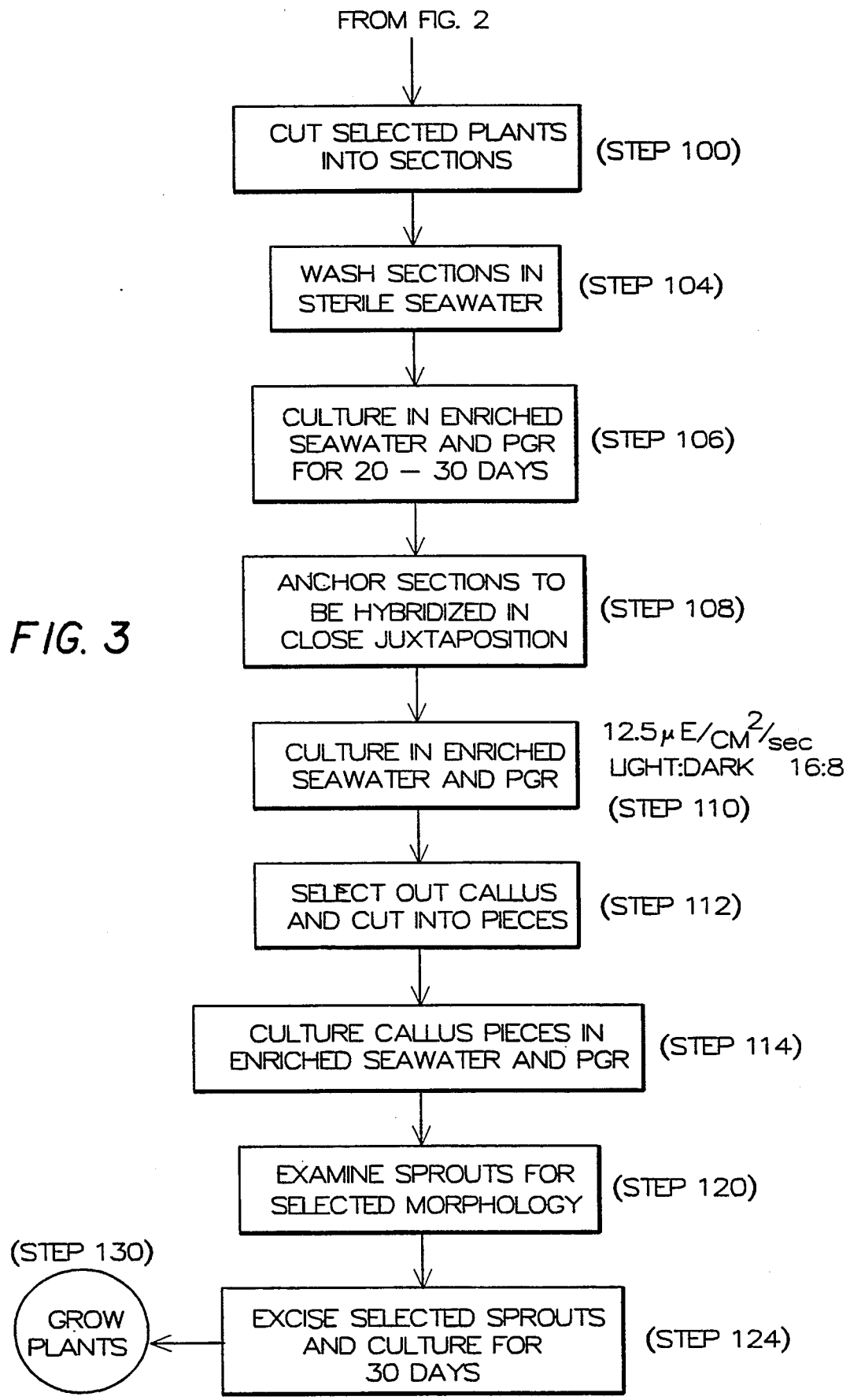
FIG. 3 is a flow chart of the steps in one embodiment of the method of the invention for the somatic cell hybridization of non-filamentous algae utilizing adjacent affixation.
Figure 3A:
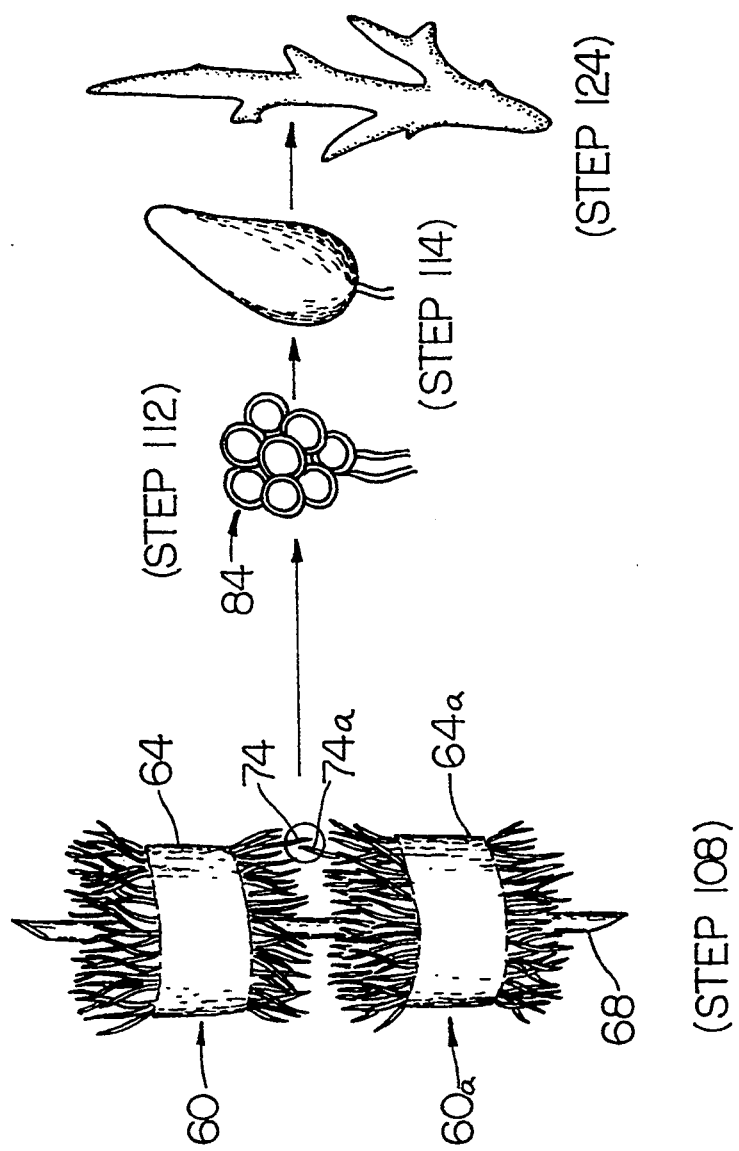
FIG. 3A is a diagrammatic representation of a number of the steps used in the embodiment of the method of somatic cell hybridization of non-filamentous algae shown in FIG. 3.

One embodiment of the method of somatic cell hybridization, referred to as close affixation is depicted in FIGS. 3 and 3a. A plant from each species to be hybridized is selected from the culture, cut into 0.3–0.6 cm long sections (step 100), and washed with sterilized seawater (step 104). These cut pieces are cultured for 20–30 days in enriched seawater (ESS/2) or ASP 12 again in the presence of plant growth regulators (step 106). At the end of the culture period, cultured pieces having a large number of cellular projections are selected from each species for hybridization.

A piece from each species 60, 60a are anchored in close juxtaposition (step 108) by placing a sharpened sterile rod 68, in one embodiment a bamboo needle, through the center of the sections 64, 64a and moving the sections 64, 64a toward one another until the sections 64, 64a are in close proximity. The sections 64, 64a are then placed in ESS/2 or ASP 12 culture medium with plant growth regulators in multiwell plates and allowed to grow at a temperature of 20° C.–24° C. in an incubator (step 110). The culture is irradiated by cool-white fluorescent light at an intensity of 12.25 $\mu$E/cm$^2$/sec with a light:dark cycle of 16:8 hours. The culture medium is changed weekly.

After about two months, projections 74, 74a grow from each section 64, 64a, and fuse forming hybrid heterokaryon callus like mass 84. The hybrid callus 84 is then cut into small pieces (step 112) and subcultured in ESS/2 or ASP 12 medium with plant growth regulators for about two months (step 114).

At the end of this time, shoots which grow from the callus are carefully observed (step 120) to identify hybrid plants. The hybrid somatic cell shoots are selected according to their morphology or pigmentation and/or by an infra-red or chemical carrageenan analysis of a crude preparation made from a portion of a potentially interesting plant. These hybrid shoots are then excised and cultured (step 124) in enriched seawater (ESS/2) for a month. Once the shoots grow to several mm in length, the shoots are placed in bubbler flasks and cultured (step 130).

Figure 4A:
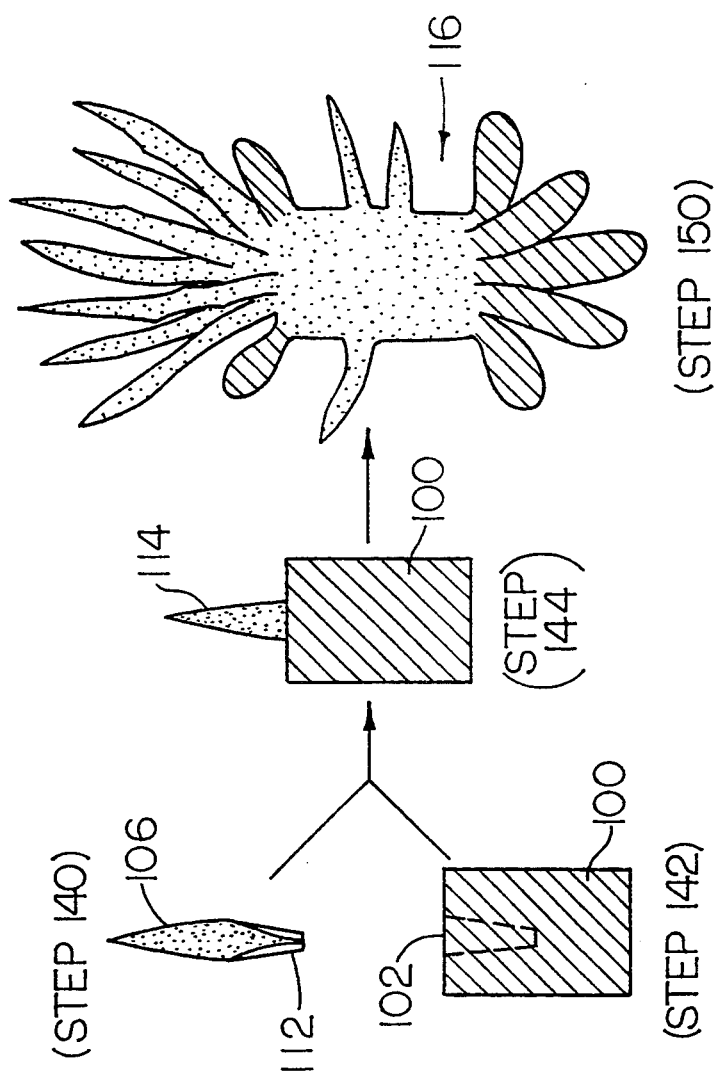
FIG. 4A is a diagrammatic representation of a number of the steps used in the embodiment of the method of somatic cell hybridization of non-filamentous algae shown in FIG. 4.

Referring to FIGS. 4 and 4a, in a second embodiment of the method of somatic cell hybridization a plant shoot from one species to be hybridized is selected from the culture and cut into a 1.0–1.5 cm long piece to form the scion 106 of the graft (step 140). The cut end of the scion 106 is further trimmed to form a wedge 112. A plant from the second species to be hybridized is selected from culture and cut into a 1.0 cm long section to form the stock 150 of the graft (step 142). A small hole 102 is made in the center or medullary tissue of the stock section 100. The width of the hole 102 is slightly wider than the diameter of the scion and the depth of the hole 102 is a little deeper than the length of the wedge portion 112 of the scion 106.

The wedge portion 112 of the scion 114 is embedded (step 144) into the hole 102 in the stock 100 deeply enough to be held. The stock section 100 and scion 106 are then placed in ASP 12 or ESS/2 culture medium in multiwell plates and allowed to grow (step 146). The media is changed weekly and the cultures permitted to grow for 3–6 months. After this time period, the graft is transferred to T25 culture flasks with ESS/2 medium. In 1–2 months, the graft is again transferred to bubbler flasks with ESS/2 medium (step 148).

The shoots 116 which form are carefully observed (step 150) to identify hybrid plants. The hybrid somatic cell shoots are selected according to their morphology or pigmentation and/or by an infra-red or chemical carrageenan analysis of a crude preparation made from a portion of a potentially interesting plant. These hybrid shoots are then excised and cultured (step 152) in enriched seawater (ESS/2). Once the shoots grow to several mm in length, the shoots are placed in bubbler flasks and cultured (step 154).

Figure 5:
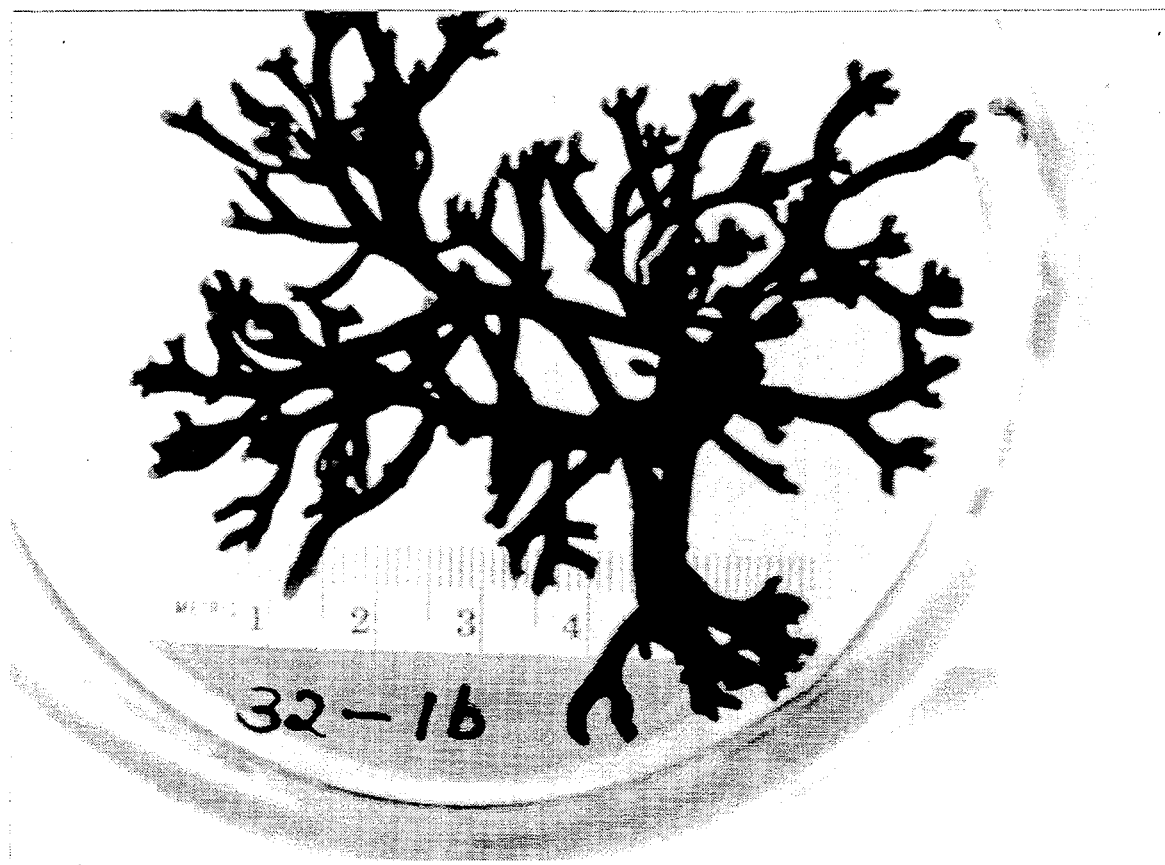
FIG. 5 is a photograph of the morphology of a hybrid of *Eucheuma spinosum* and *Eucheuma* (*E.*) *cottonii* made by the method of the invention.

The criteria (morphological, pigmentation, chemical analysis of plant components or infra-red or chemical analysis of the carrageenan produced) by which hybrid shoots are selected for culture are determined by the characteristics (morphological, pigmentation, chemical analysis of plant components or infra-red or chemical analysis of the carrageenan produced) of the species being hybridized. For example, the hybridization of a red algal species and a greenish pigmented red algal species might result in a hybrid shoot which is reddish green. Similarly, the hybridization of an alga which has spiny features, such as *Eucheuma spinosum*, with a alga which has smooth features, such a *E. cottonii*, might result in shoots having a morphology which is intermediate between smooth and spiny features. A photograph of such a hybrid is shown in FIG. 5.

Figure 6:
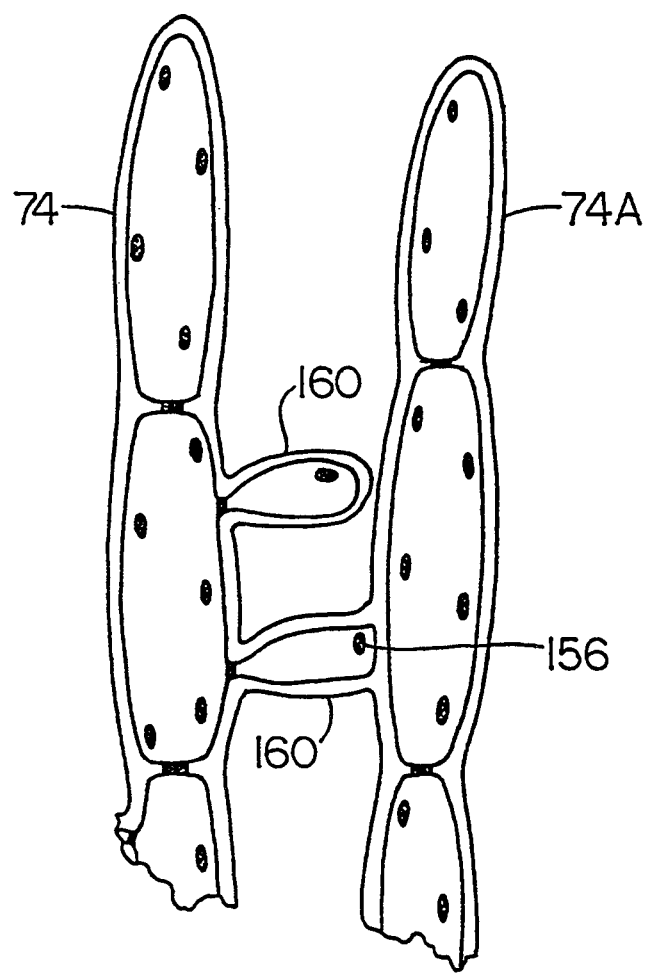
FIG. 6 is a diagrammatical representation of hybrid generation by way of conjunctor cell formation.

The mechanism by which the hybrid somatic cells form is not completely understood. It is believed (as shown in FIG. 6) that hybrid somatic cells form as the result of the transfer of nuclei 156 from projections 74 of one species to projections 74a of the other species by way of a conjunctor cell 160. Nuclear exchange has been observed microscopically using the nuclear stain DAPI. Evidence that hybrid cells are formed may be demonstrated by isozyme protein electrophoresis, by the morphological characteristics of the plants and by the presence of the cytoplasmic incompatibility reaction (CIR) which occurs in sensitive species as a result of cell fusion. Additionally, the hybrid plants may produce phycocolloids which have a different gel strength from the phycocolloids produced by either of the parent species.

Figure 7:
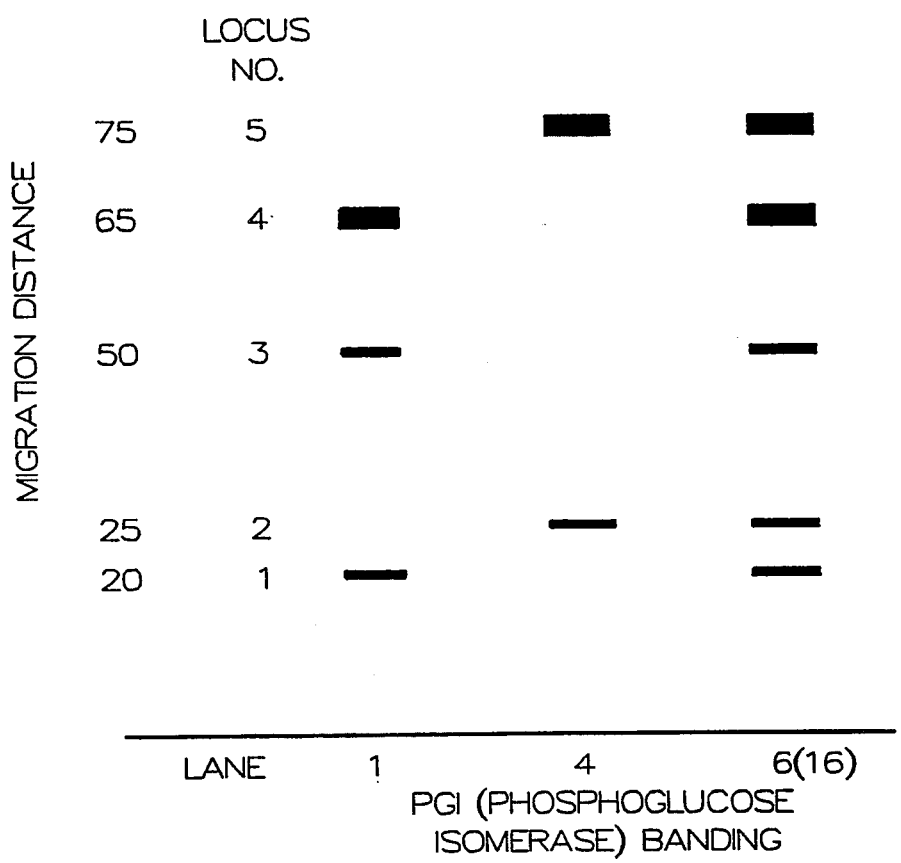
FIG. 7 is a graphical representation of the electrophoretic mobility of the enzyme phosphoglucose isomerase for *Eucheuma spinosum*, *E. cottonii*, and the hybrid alga made by the method of the invention as shown in FIG. 5.

An example of the chemical analysis of the plant components of a hybrid which may be considered to be illustrative of hybridization is shown in FIG. 7. In this example, the electrophoresis of the isoenzymes of phosphoglucose isomerase (PGI) from a hybrid of *Eucheuma spinosum* and *E. cottonii*, designated as E32-1b, is compared to the isoenzymes of PGI isolated from the parental stock species from which the hybrid was derived. Lane 1 shows the migration distance of the isoenzymes of PGI from *E. cottonii*. Lane 4 shows the migration distance of the isoenzymes of PGI from *Eucheuma spinosum*, and lane 6(16) shows the migration distance of the isoenzymes of PGI from a hybrid of *Eucheuma spinosum* and *E. cottonii* designated as E32-1b. As is easily seen, the isozyme pattern of the hybrid is a combination of the isozyme patterns of the species of plants from which it was derived.

Additionally, a microanalytical infra-red technique may be used to screen potential hybrids for culture by comparing the relative sulfation of the carrageenan produced by each suspected hybrid to the amount of sulfation of the carrageenan produced by each parent species. The microanalytical infra-red technique may be performed on as little as 150–200 mg fresh weight (or 11–15 mg dry weight) of sample. The sample of the suspected hybrid is placed in 2 ml of $H_2O$ and heated to 90° C. for four hours. The resulting mixture is cooled to 60° C. and filtered using Mirocloth. The solution which passes through this filter may be again filtered using a 5μ filter. The resulting carrageenan extract is poured into a mold and allowed to dry overnite at 50° C. into a film. The film is then mounted for use and its spectrum taken in an infra-red spectrometer.

Table 1 lists various peaks in the IR spectra of phycocolloids. The ratio of the intensity of the various bands of the spectra can be used to determine the chemical consituents of the phycocolloids. For example, the ratio of the intensity of the various bands of the spectrum of carrageenan can be used to determine the relative amount of sulfation of the carrageenan and hence provide an indication of the carrageenan's gel strength. Specifically, the ratio of the intensity of the 805 $cm^{-1}$ band of the infra-red spectrum which is generated by the amount of sulfate at the 3,6-anhydro-galactose 2-sulfate position of $\iota$ carrageenan to the intensity of the 850 $cm^{-1}$ band of the infra-red spectrum which is generated by the amount of sulfate at the galactose-4-sulphate position of $\iota$ and $\kappa$ carrageenan has been shown to be inversely related to the gel strength of the carrageenan. Thus by comparing the ratio of the 805 $cm^{-1}$/850 $cm^{-1}$ bands as produced by the suspected hybrid with the ratio as produced by each of the parents, hybrids producing an increased or different gel strength carrageenan from that produced by the parents' species can be selected. Additionally, the 830 $cm^{-1}$ is indicative of the amount of sulfation of $\lambda$ carrageenan. It should be noted that other bands in the infra-red spectrum of carrageenan have been used to indicate the amount of sulfation and that other bands may be used to determine the properties of other phycocolloids, such as agar.

Figure 8:
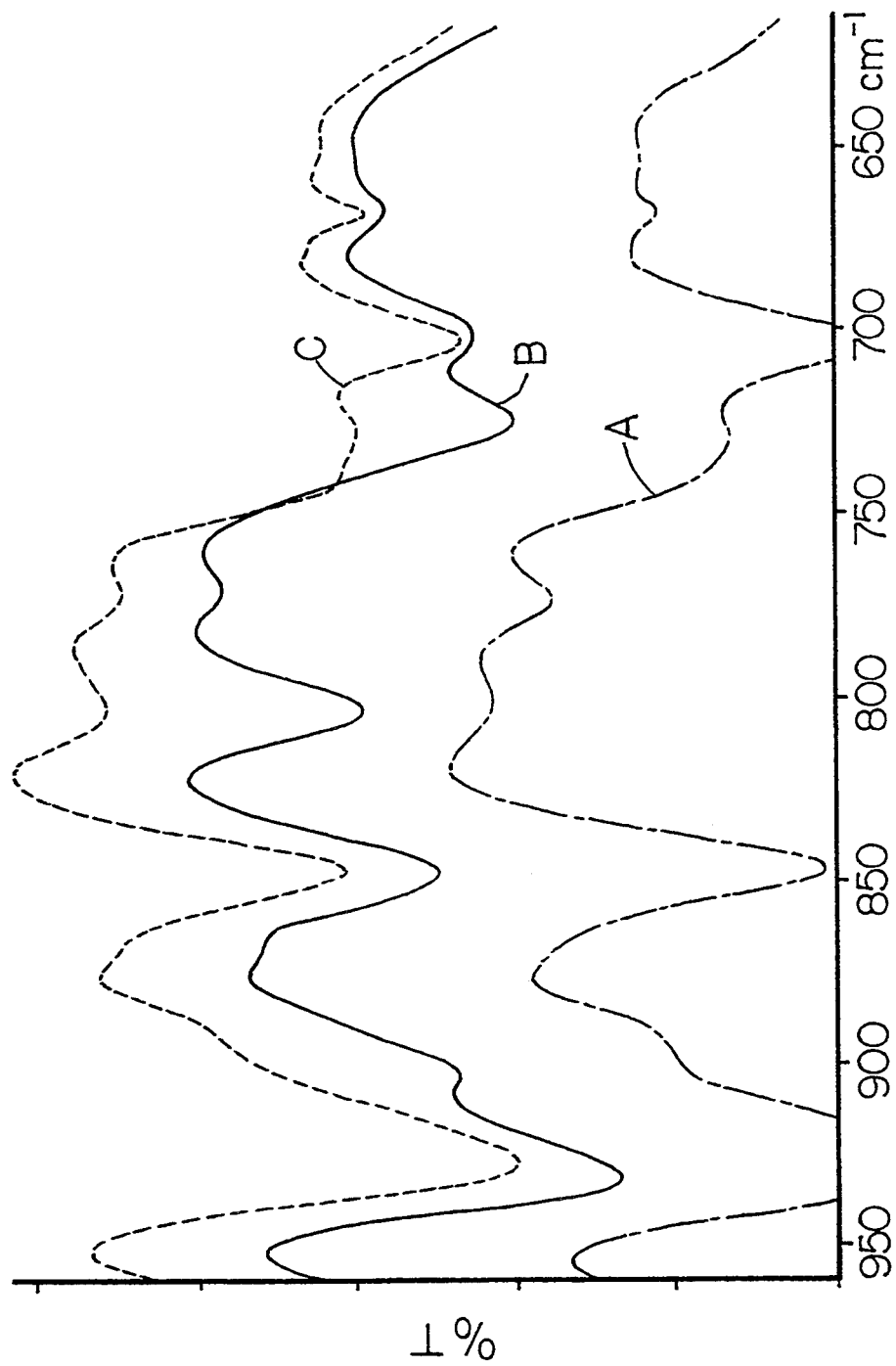
FIG. 8 depicts an infra-red spectrum taken of carrageenan produced by *E. cottonii*, *Eucheuma spinosum* and an infra-red spectrum taken of carrageenan produced by a hybrid made by the method of the invention.

FIG. 8 depicts infra-red spectra of carrageenan produced by *E. cottonii* (Curve A) and *Eucheuma spinosum* (Curve B), taken by the above described microanalytical infra-red method and an infra-red spectrum (curve C) of carrageenan produced by a hybrid designated as E34-1'a-j. The hybrid E34-1'a-j was formed using the close affixation method of the first embodiment by closely affixing an *E. cottonii* parent species and an *Eucheuma spinosum* parent species.

The ratio of the 805 $cm^{-1}$ band to the 850 $cm^{-1}$ band for the carrageenan produced by *E. cottonii* is 0.085 while the ratio of the 805 $cm^{-1}$ band to the 850 $cm^{-1}$ band for carrageenan produced by E34-1'a-j is 0.165, indicating a significantly different degree of sulfation and hence a true hybrid. Additionally, since the hybrid has a greater 805 $cm^{-1}$ peak than *E. cottonii*, it would be expected to have a lower gel strength.

An analysis of the gel strength and gelling temperature for the carrageenan produced by the hybrid E34-1'a-j confirms the IR data discussed above. The carrageenan produced by the hybrid E34-1'a-j has a gel strength of 2510 pascals at 10° C. as measured by rheometer and a gelling temperature of 37° C. This is significantly different from the parent species *E. cottonii* which produces carrageenan which has a gel strength which ranges from 5,500–7,000 pascals and *Eucheuma spinosum* which produces carrageenan which has a gel strength of less than 200 pascals. Therefore, hybrid E34-1'a-j , which can be farmed in the tropics like *E. cottonii*, produces a carrageenan having a gel strength similar to that of carrageenan produced by *Chondrus crispus* (1,700–3,400 pascals), which can not be farmed in the tropics like *E. cottonii.*

It should be noted that the number of viable hybrids produced from a series of attemped hybridizations may be increased by the use of healthy, uncontaminated, and laboratory grown plants as the stock species from which the hybrid is created.

These and other examples of the concept of the invention illustrated above are intended by way of example and the actual scope of the invention is to be determined solely from the following claims.

TABLE 1

SIGNIFICANT BANDS IN THE INFRA-RED SPECTRA OF PHYCOCOLLOIDS

| WAVENUMBER $CM^{-1}$ | SOURCE MOIETY | PHYCOCOLLOID |
|---|---|---|
| 805 | 3,6-anhydro-galactose-2-sulfate | l carrageenan |
| 820 | galactose-6-sulfate | k, l carrageenan precursor |
| 830 | galactose-2-sulfate | λ carrageenan |
| 845–850 | galactose-4-sulfate | k,l carrageenan |
| 930 | 3,6-anhydro-galactose | k carrageenan |
| 1370 | total sulfate | carrageenan and agar |
| 2920 | total sugar content | carrageenan and agar |

We claim:

1. A non-filamentous hybrid alga formed from somatic cell hybridization of *Eucheuma cottonii* and *Eucheuma spinosum* by a method of hybridization comprising the steps of:
   removing a section from each said *Eucheuma cottonii* and *Eucheuma spinosum* algal species to be hybridized;
   anchoring, in close juxtaposition, each said section from each of said *Eucheuma cottonii* and *Eucheuma spinosum* algal species to be hybridized;
   culturing said sections in close juxtaposition until projections from each section have fused with projections from each said other section to form hybrid new shoots; and
   isolating said hybrid new shoots so formed,
   said non-filamentous hybrid algae producing a carrageenan having a gel strength of about 2500 pascals at 10° C. as measured by rheometer and a gelling temperature of about 37° C.

2. A method for somatic cell hybridization of *Eucheuma cottonii* and *Eucheuma spinosum* by a method of hybridization comprising the steps of:
   removing a section from each said *Eucheuma cottonii* and *Eucheuma spinosum* to be hybridized;
   anchoring, in close juxtaposition, each said section from each of said *Eucheuma cottonii* and *Eucheuma spinosum* to be hybridized;
   culturing said sections in close juxtaposition until projections from each said section have fused with projections from each said other section to form hybrid new shoots; and
   isolating said hybrid new shoots so formed.

3. A method for somatic cell hybridization of *Eucheuma cottonii* and *Eucheuma spinosum* comprising the steps of:
   removing a stock section from one of *Eucheuma cottonii* and *Eucheuma spinosum* to be hybridized;
   removing a tip from the other of *Eucheuma cottonii* and *Eucheuma spinosum;*
   cutting said tip to make an insertion portion to said tip;
   embedding said insertion portion of said tip into said stock section;
   culturing said tip and said stock section until hybrid new shoots grow from said stock section and tip; and
   isolating said hybrid new shoots so formed.

4. A non-filamentous hybrid alga formed from somatic cell hybridization of *Eucheuma cottonii* and *Eucheuma spinosum,* by a method of hybridization comprising the steps of:
   removing a section from each said *Eucheuma cottonii* and *Eucheuma spinosum;*
   anchoring, in close juxtaposition, each said section from each of said *Eucheuma cottonii* and *Eucheuma spinosum;*
   culturing said sections in close juxtaposition until projections from each section have fused with projections from each said other section to form hybrid new shoots; and
   isolating said hybrid new shoots so formed,
   said non-filamentous hybrid algae producing phycocolloid having properties different from said properties of phycocolloid produced by either two non-filamentous algae.

5. A non-filamentous hybrid alga formed from somatic cell hybridization of *Eucheuma cottonii* and *Eucheuma spinosum,* by a method of hybridization comprising the steps of:
   removing a stock section from one of *Eucheuma cottonii* and *Eucheuma spinosum;*
   removing a tip from the other of *Eucheuma cottonii* and *Eucheuma spinosum;*
   cutting said tip to make an insertion portion to said tip;
   embedding said insertion portion of said tip into said stock section;
   culturing said tip and said stock section until hybrid new shoots grow form said stock section and tip; and
   isolating said hybrid new shoots so formed.

6. A method for somatic cell hybridization of two non-filamentous anatomically complex, thallophytic marine red algal plants comprising the steps of:
   removing a section from each said non-filamentous anatomically complex, thallophytic marine red algal plant to be hybridized;
   anchoring, in close juxtaposition, each said section from each of said non-filamentous anatomically complex, thallophytic marine red algal plant to be hybridized;
   culturing said sections in close juxtaposition until projections from each said section have fused with projections from each said other section forming hybrid new shoots; and
   isolating said hybrid new shoots so formed.

7. A method for somatic cell hybridization of two non-filamentous anatomically complex, thallophytic marine red algal plants comprising the steps of:
   removing a stock section from one non-filamentous anatomically complex, thallophytic marine red algal plant to be hybridized;
   removing a tip from a second said plant;
   cutting said tip to make an insertion portion to said tip;
   embedding said insertion portion of said tip into said stock section;
   culturing said tip and said stock section until hybrid new shoots grow from said stock section and tip; and
   isolating said hybrid new shoots so formed.

8. A non-filamentous hybrid alga formed from somatic cell hybridization of two non-filamentous anatomically complex, thallophytic marine red algal plants, by a method of hybridization comprising the steps of:
- removing a section from each said non-filamentous anatomically complex, thallophytic marine red algae plant to be hybridized, wherein each of said red algal plants is of a different species than the other;
- anchoring, in close juxtaposition, each said section from each of said non-filamentous anatomically complex, thallophytic marine red algal plant to be hybridized;
- culturing said sections in close juxtaposition until projections from each said section have fused with projections from each said other section to form hybrid new shoots; and
- isolating said hybrid new shoots so formed,
- said non-filamentous hybrid algae producing phycocolloid having properties different from properties of phycocolloid produced by either two non-filamentous algal plants.

9. A non-filamentous hybrid alga formed from somatic cell hybridization of two non-filamentous anatomically complex, thallophytic marine red algal plants, wherein each of said red algal plants is of a different species than the other, by a method of hybridization comprising the steps of:
- removing a stock section from one non-filamentous anatomically complex, thallophytic marine red algae plant to be hybridized;
- removing a tip from a second plant;
- cutting said tip to make an insertion portion to said tip;
- embedding said insertion portion of said tip into said stock section;
- culturing said tip and said stock section until hybrid new shoots grow from said stock section and tip; and
- isolating said hybrid new shoots so formed.

* * * * *

UNITED STATES PATENT AND TRADEMARK OFFICE
CERTIFICATE OF CORRECTION

PATENT NO. : 5,365,018
DATED : November 15, 1994
INVENTOR(S) : Donald P. Cheney
Le Z. Wang It is certified that error appears in the above-indentified patent and that said Letters Patent is hereby corrected as shown below:

Table 1, Column 7, line 13, "l carrageenan" should read --ι carrageenan--.

Table 1, Column 7, line 15, "k,l carrageenan" should read --κ,ι carrageenan--.

Table 1, Column 7, line 17, "k,l carrageenan" should read --κ,ι carrageenan--.

Table 1, Column 7, line 18, "k carrageenan" should read --κ carrageenan--.

Column 8, line 36, "form" should read --from--.

Signed and Sealed this

Twenty-eighth Day of July, 1998

Attest:

BRUCE LEHMAN

Attesting Officer     Commissioner of Patents and Trademarks